(12) United States Patent
Schubert et al.

(10) Patent No.: US 8,903,045 B2
(45) Date of Patent: Dec. 2, 2014

(54) BACKSCATTER SYSTEM WITH VARIABLE SIZE OF DETECTOR ARRAY

(75) Inventors: Jeffrey R. Schubert, Somerville, MA (US); William Randall Cason, Danvers, MA (US)

(73) Assignee: American Science and Engineering, Inc., Billerica, MA (US)

( * ) Notice: Subject to any disclaimer, the term of this patent is extended or adjusted under 35 U.S.C. 154(b) by 417 days.

(21) Appl. No.: 13/446,521

(22) Filed: Apr. 13, 2012

(65) Prior Publication Data

US 2012/0263276 A1 Oct. 18, 2012

Related U.S. Application Data

(60) Provisional application No. 61/475,994, filed on Apr. 15, 2011.

(51) Int. Cl.
G01N 23/203 (2006.01)
G01N 23/201 (2006.01)

(52) U.S. Cl.
CPC .................................. *G01N 23/203* (2013.01)
USPC ........................... 378/86; 378/70; 370/370.09

(58) Field of Classification Search
USPC ..................... 378/58, 70, 86–89, 196–198; 250/370.08, 370.09
See application file for complete search history.

(56) References Cited

U.S. PATENT DOCUMENTS

| | | | |
|---|---|---|---|
| 5,754,683 A | 5/1998 | Hayashi et al. | 382/167 |
| 5,904,468 A * | 5/1999 | Dobler et al. | 415/55.2 |
| 6,292,533 B1 | 9/2001 | Swift et al. | 378/57 |
| 6,424,695 B1 | 7/2002 | Grodzins et al. | 378/87 |
| 7,508,910 B2 | 3/2009 | Safai et al. | 378/57 |
| 7,542,547 B2 * | 6/2009 | Kogan | 378/81 |
| 7,551,715 B2 * | 6/2009 | Rothschild et al. | 378/57 |
| 8,094,783 B2 * | 1/2012 | Harding | 378/88 |
| 2007/0098142 A1 * | 5/2007 | Rothschild et al. | 378/57 |
| 2008/0008292 A1 * | 1/2008 | Krmar et al. | 378/89 |
| 2011/0075808 A1 * | 3/2011 | Rothschild et al. | 378/88 |
| 2011/0081003 A1 * | 4/2011 | Harding | 378/88 |
| 2013/0054153 A1 * | 2/2013 | Motl et al. | 702/28 |
| 2013/0101091 A1 * | 4/2013 | Garvey et al. | 378/87 |

OTHER PUBLICATIONS

Authorized Officer: Jihun Cho Notification of Transmittal of the International Search Report and the Written Opinion of the International Searching Authority, or the Declaration, PCT/US2012/033585; Date of Mailing: Nov. 29, 2012, 11 pages.

* cited by examiner

*Primary Examiner* — Bernard E Souw
(74) *Attorney, Agent, or Firm* — Sunstein Kann Murphy & Timbers LLP

(57) ABSTRACT

A variable-geometry backscatter inspection system has a radiation detector array including one or more backscatter radiation detectors. The position of a second backscatter radiation detector is variable with respect to the position of a first backscatter radiation detector, so that the size of the detector array may be varied by moving the second radiation detector into or out of a predefined alignment with the first radiation detector. The system may include a movable base, and at least one of the detectors is movable with respect to the base. Methods of inspecting an object include forming a detector array by moving a second radiation detector into a predefined alignment with a first radiation detector, illuminating the object with a pencil beam of penetrating radiation, and detecting backscattered radiation with the detector array.

20 Claims, 11 Drawing Sheets

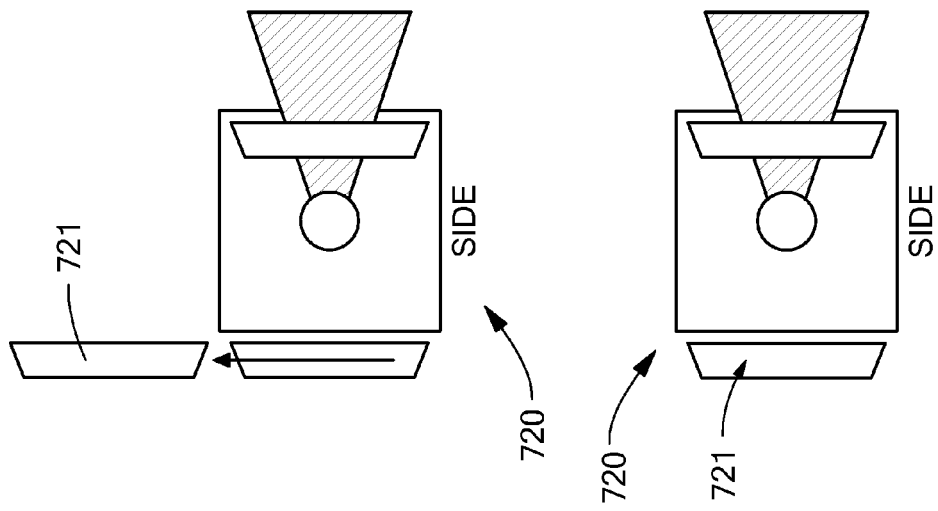
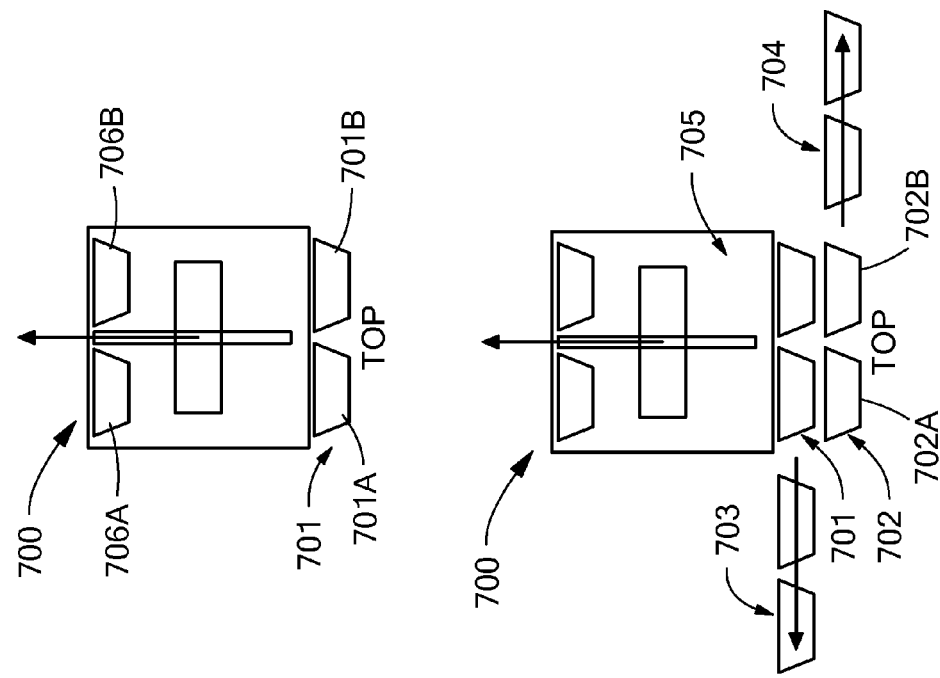
FIG. 7B
FIG. 7A

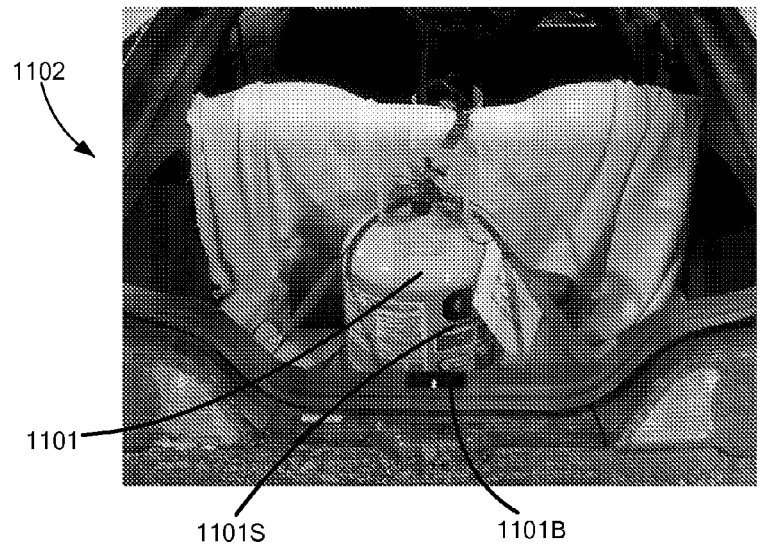
FIG. 11A
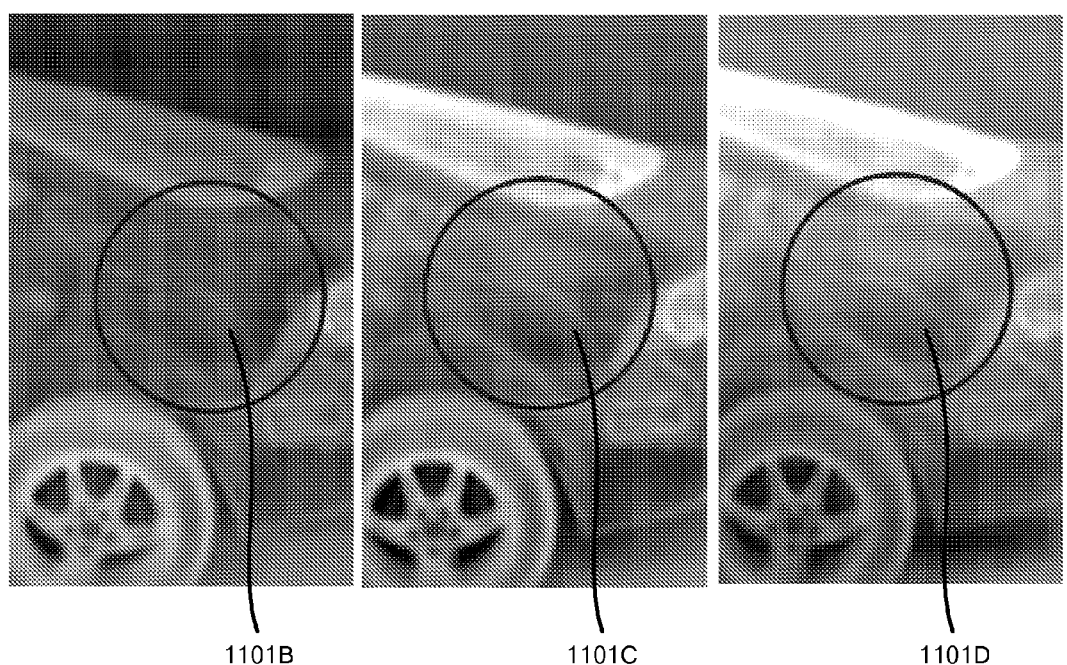
FIG. 11B  FIG. 11C  FIG. 11D

BACKSCATTER SYSTEM WITH VARIABLE SIZE OF DETECTOR ARRAY

TECHNICAL FIELD

This patent application claims priority from provisional U.S. patent application No. 61/475,994, filed Apr. 15, 2011, entitled, "Backscatter System with Variable Size Detector Array" and naming Jeffrey R. Schubert and William Randall Cason as inventors, the disclosure of which is incorporated herein, in its entirety, by reference.

TECHNICAL FIELD

The present invention relates to detector arrays, and more particularly to arrays for detecting backscattered penetrating radiation such as x-rays.

BACKGROUND ART

It is known in the prior art to inspect an object by illuminating it with penetrating radiation. Some of the radiation may pass through the object, and some may be absorbed or deflected by the object. Some of the illuminating radiation, however, will be scattered in all directions, such as back in the general direction from which it came, in which case the scattered radiation may be referred to as backscatter radiation. Such scattered radiation may pass into a detector (which may be referred to, herein, as a "scatter detector," and some portion of that scattered radiation will be detected by the detector.

Existing systems for inspection of objects, for security applications, for example, employ scatter detectors that are fixed in position relative to the beam of illuminating radiation, or that, upon reorientation, subtend substantially the same solid angle with respect to the inspected object as before reorientation. One such system with reconfigurable scatter detectors is shown in FIGS. 5A and 5B of U.S. Pat. No. 5,764,683. Such inspection systems, however, are designed for inspection, at specified range, on the order of a meter, of a particular class of objects (namely, cars and trucks), which are inspected at a substantially fixed distance with respect to the inspection system. Such inspection systems cannot provide for substantial variation in the footprint of the detector array when called upon for inspection in particularly close quarters, or so as to accommodate substantial variation in the distance between the inspection system and the inspected object. The latter might be necessary in a field deployment, where the inspected object may be disposed at a substantial distance from the inspection system.

SUMMARY OF THE EMBODIMENTS

In a first embodiment a variable geometry backscatter inspection system for inspecting a surface of an object, the system includes a conveyance configured to move along a line of travel; a source of a pencil beam of penetrating radiation, the source coupled to the conveyance and having an axis of emission; a variable geometry detector array that includes a first detector coupled to the conveyance and having a first alignment vector, the first alignment vector parallel to the line of travel, and a second detector movably coupled to the conveyance and having a second alignment vector, the second detector movable between a first position and a second position, wherein the second alignment vector is parallel to the line of travel in the first position, such that the array presents a first solid angle when viewed from a point on the line of travel when the second detector is in the first position, and a smaller solid angle when the second detector is in the second position.

In some embodiments, the second detector movably coupled to the conveyance by a movable member. In some embodiments the movable member includes and arm having a first end rotatably coupled to the conveyance, and a second end coupled to the second detector.

In some embodiments, the second detector includes a first unit and a second unit, the second unit foldable to face the first unit.

In some embodiments, wherein the movable member includes a detector frame defining the second alignment vector parallel to the first alignment vector, and movable with respect to the conveyance such that the second alignment vector remains parallel to the first alignment vector in both the first and second position. In some embodiments, the detector frame is adapted for motion parallel to a surface on which the conveyance is located, while in some embodiments the detector frame is adapted for motion perpendicular to a surface on which the conveyance is located, and in some embodiments the detector frame is adapted for motion diagonally with respect to a surface on which the conveyance is located.

In another embodiment, a variable geometry backscatter inspection system for inspecting a surface of an object includes a conveyance; a source of a pencil beam of penetrating radiation, the source coupled to the conveyance; a primary detector coupled to the conveyance, the primary detector having a first location relative to the radiation source and a first alignment vector; a movable member movably coupled to the conveyance; and a secondary detector coupled to the movable member, the secondary detector having a second alignment vector, such that the alignment vector of the secondary detector is configured for reorientation with respect to the alignment vector of the primary detector in such a manner that the sensitivity of the system to radiation scattered from the object is substantially maximized when the first and second alignment vectors are substantially parallel.

In some embodiments, the movable member includes an arm, and the arm includes a first end rotatably coupled to the conveyance, and a second end coupled to the secondary detector, such that the arm rotatable between an open position in which the second alignment vector is parallel to the first alignment vector, and a retracted position in which the second alignment vector is not parallel to the first alignment vector.

In some embodiments, the second alignment vector is perpendicular to the first alignment vector when the second end is in the retracted position.

In some embodiments, the secondary detector includes a first unit and a second unit, the second unit foldable to face the first unit.

In some embodiments, the movable member includes a detector frame defining a secondary alignment vector parallel to the first alignment vector and movable with respect to the conveyance such that the secondary alignment vector remains parallel to the first alignment vector.

In some embodiments, the detector frame is adapted for motion parallel to a surface on which the conveyance is located, and in some embodiments, the detector frame is adapted for motion perpendicular to a surface on which the conveyance is located, and in some embodiments, the detector frame is adapted for motion diagonally with respect to a surface on which the conveyance is located.

In another embodiment, a method for inspecting an object with backscatter radiation, the method includes the steps of providing a conveyance comprising a source of a pencil beam of penetrating radiation; providing a first detector of backscatter radiation, the first detector having a fixed position relative to the conveyance, and the first detector having a first alignment vector; providing a second detector of backscatter radiation, the second detector movably coupled to the conveyance, and the second detector having a second alignment vector; orienting the second detector such that the second alignment vector intersects the first alignment vector; illuminating the object with a pencil beam of radiation from the source; detecting radiation scattered by the source with the first detector and the second detector; generating a first image of the object using data representing the radiation scattered by the source and detected by the first detector; and generating a second image of the object using data representing the radiation scattered by the source and the second detector.

In some embodiments, the method also includes producing a compound image by combining data from the first image with data from the second image.

In some embodiments, the step of producing a compound image by combining data from the first image with data from the second image includes producing a dynamically variable image by adjusting the proportion of the first image and the proportion of second image combined to produce the compound image.

In some embodiments, the step of orienting the second detector such that the second alignment vector intersects the first alignment vector comprises orienting the second detector such that the second alignment vector intersects the first alignment vector the angle at a right angle.

BRIEF DESCRIPTION OF THE DRAWINGS

The foregoing features of embodiments will be more readily understood by reference to the following detailed description, taken with reference to the accompanying drawings, in which:

FIG. 7A and FIG. 7B schematically illustrate embodiments of variable geometry backscatter inspection systems;

FIGS. 11A-11D are digital images of an object, and various images of that object produced by an embodiment of a variable geometry backscatter inspection system;

DETAILED DESCRIPTION OF ILLUSTRATIVE EMBODIMENTS

In accordance with illustrative embodiments, an array of detectors is configured to present a detector of backscatter radiation with variable geometry. To that end, a detector array has a number of detectors of backscattered radiation ("detectors") that can change positions or orientations with respect to one another.

Figure 1:
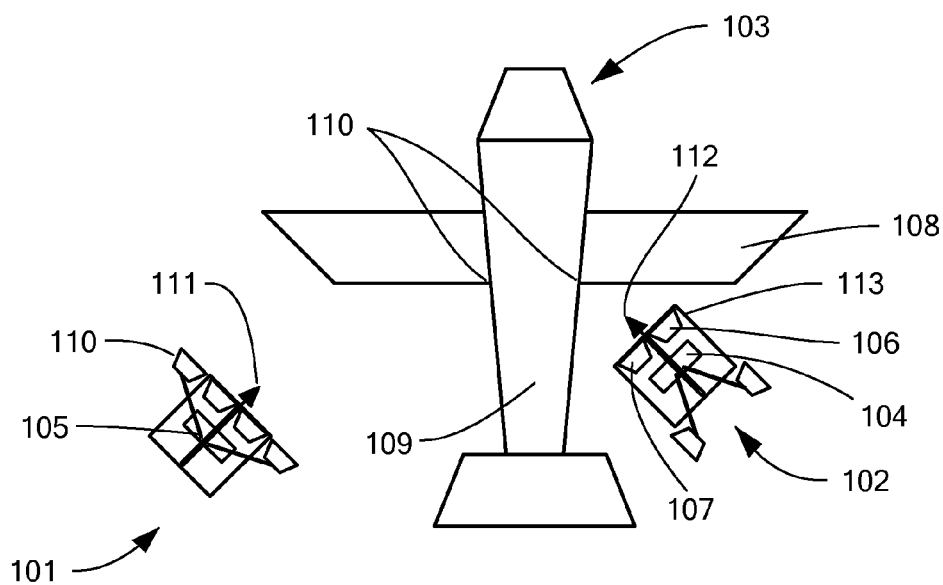
FIG. 1 schematically illustrates two variable geometry backscatter inspection systems positioned adjacent to an airplane.

FIG. 1 schematically illustrates two backscatter detector systems 101 and 102 adjacent to a small aircraft 103. Each of the backscatter detector systems 101 and 102 includes a source of penetrating radiation 104, 105 respective pointed at the aircraft 103. Each source 104, 105, may produce a narrow beam of penetrating radiation, which may be known as a pencil beam of penetrating radiation. In fact, systems 101 and 102 are identical, but are configured differently in FIG. 1.

System 102 will be described in detail below, with the understanding that system 101 has the same components. As shown in FIG. 1, the ability to configure the backscatter detector systems 101 and 102 allows system 102 to be configured so that its detector array presents a smaller profile than the array in system 101. As such, system 102 is able to move closer to the plane 103 in the tight space between the wing 108 and fuselage 109. This ability extends the scope of useful applications for the system 102.

In operation of system 102, the source 104 illuminates the aircraft 103 with penetrating radiation, and a portion of that illuminating radiation (the "scattered" or "backscattered" radiation) is scattered back in the general direction of the source. Unlike the pencil beam of penetrating radiation, the scattered radiation is omnidirectional. As such, some of the scattered radiation passes into the detectors 106 and 107, which together form detector array 113. Some of that backscattered radiation may pass through the detectors 106 and 107 undetected, while some of the backscattered radiation will be detected by those detectors.

Generally, the greater the solid angle of the detector or detectors as measured from a point of scatter, the more likely that the backscattered radiation will be detected. Thus, the dimensions of the detector (or an array of detectors) may influence a system's sensitivity.

Accordingly, in describing various embodiments and in any claims appended hereto, the following definition may be employed: the term "alignment vector," when used with respect to a detector of scattered radiation, shall refer to a direction defined by a linear locus of points extending outward from the detector, with respect to which the solid angle subtended by the volume of the detector as seen from an observation point on the linear locus of points exceeds the solid angle as seen from any other point in a plane, which plane is transverse to the vector at the observation point.

In various embodiments described herein, the alignment vectors of various radiation detectors are parallel to the alignment vectors of other detectors, and/or parallel to the transmission axis of pencil beam of penetrating radiation. While such an orientation may maximize the total sensitivity of the respective arrays, this is not a required limitation. For example, if less than 100 percent sensitivity from a given detector within an array of detectors is sufficient for a given application, the respective alignment vectors may be oriented at an angle greater than zero (i.e., the vectors are not parallel). Therefore, in some embodiments an "alignment vector" can refer to a line that intersects a locus of points as described above at a fixed, pre-determined angle.

Figure 2:
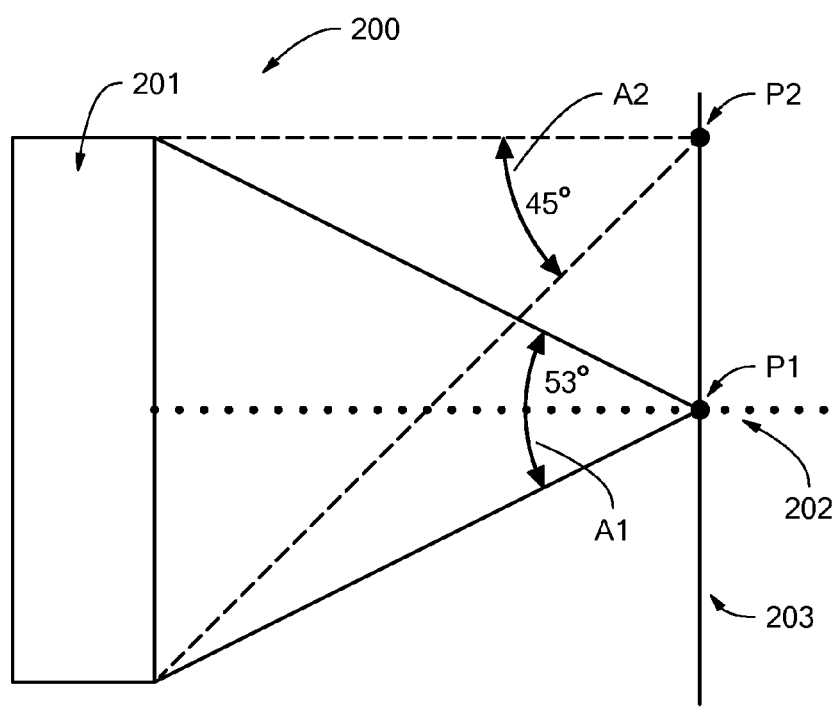
FIG. 2 schematically illustrates a radiation detector and an alignment vector.

For example, a cross-section 200 of a detector of penetrating radiation 201 is schematically illustrated in FIG. 2. Point P1 is in the plane of the cross-section and on a locus of points 202 extending outward from the detector 201. Radiation scattering (e.g., backscattering) from point P1 in the plane of the cross-section 200 will reach the detector 201 if the backscattered radiation is within the 53 degree arc A1. In other words, all radiation within the plane of the cross-section 200 and within the arc A1 will pass into the detector 201, and thereby provide an opportunity for detector 201 to detect it. In this sense, point P1 may be considered a point source of radiation, even though in fact it is a point from which impinging radiation is scattered. As such, it is not necessary to specify the ultimate source of the penetrating radiation.

In contrast, radiation scattering from point P2, which is on a plane 203 transverse to the locus of points 202 at point P1 (in FIG. 2, the plane is perpendicular to the cross-section, and therefore appears as a line), will only reach detector 201 if it scatters within the 45 degree arc A2.

Thus, the solid angle subtended by the volume of the detector 201 as seen from point P1 is larger than the solid angle subtended by the volume of the detector 201 as seen from point P2.

In fact, of all the points in plane 203, none will present a solid angle subtended by the volume of the detector 201 larger than the solid angle presented from point P1. As such, the locus of points 202 is the alignment vector in accordance with the foregoing definition.

Figure 3:
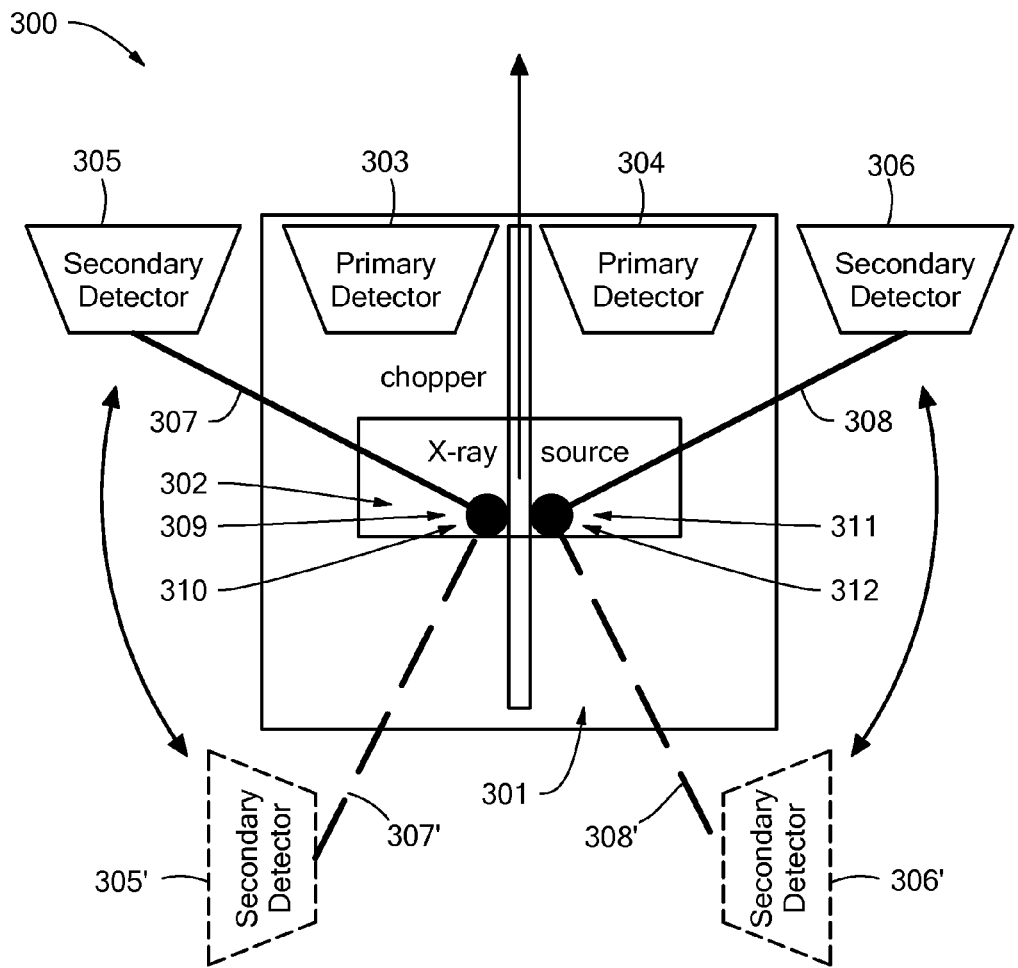
FIG. 3 schematically illustrates an embodiment of a variable geometry backscatter inspection system.

One embodiment of a backscatter detector system 300 is schematically illustrated in FIG. 3, and includes a base, or conveyance 301, which supports the other elements of the system. In this figure, the system 300 is resting on the ground and viewed from a point above the system looking down.

The conveyance 301 may be adapted for ease of mobility, and to that end may have wheels or tracks to engage the surface on which the system is placed. Alternately, the conveyance 301 may be a platform coupled to a base, such that the platform can move independently of the base.

The system 300 also has an X-ray source 302, which may produce a pencil-beam of penetrating radiation as described above. In this embodiment, the X-ray source 302 is coupled to the conveyance 301 so that the X-ray source bears a fixed spatial relationship to the conveyance 301. In operation, therefore, illuminating an object involves moving the conveyance 301 so that the X-ray source 302 points in the direction of the object.

The system 300 also includes two detectors, 303 and 304, each of which has an associated alignment vector. These detectors, 303 and 304, which may be known as the "primary detectors," are coupled to the conveyance 301 such that they each bear a fixed spatial relationship to the conveyance 301. Together, the primary detectors 303 and 304 form an array of detectors.

In operation, some of the radiation produced by X-ray source 302 will be scattered by the illuminated object back in the general direction of the detectors 303 and 304, and will consequently be detected by the detectors.

In some embodiments, data representing the detected backscatter radiation is then provided to a computer (not shown), and processed using specialized software to produce an image of the object. To that end, the system may have one or more data communication channels to convey digitized data to a memory or computer processor. Detected radiation may be digitized and transmitted to a microprocessor or using a data communication channel.

The sensitivity of the system 300 will be defined, at least in part, by the detectors 303 and 304. However, some of the backscattered radiation will escape detection by detectors 303 and 304 because it passes wide of those detectors. In other words, radiation backscattering from a point on the object may scatter at an angle outside the solid angle presented by the volume of the detectors 303 and 304 as seen from that point. As such, the sensitivity of the system 300 may be enhanced by controllably adding additional detectors to increase the solid angle of the array of detectors as seen from the point of backscatter. Such a system may be known as a variable geometry backscatter detection system.

To that end, the system 300 has two additional detectors, 305 and 306. These may be known as "secondary" detectors or "auxiliary" detectors. In this embodiment, the secondary detectors 305 and 306 are movably coupled to the conveyance 301 by respective arms 307 and 308. Thus, although the secondary detectors 305 and 306 are coupled to the conveyance 301, they do not bear a fixed special relationship to the conveyance because their position is variable. Secondary detector 305, arm 307, pivot joint 309, and pivot point 310 will be described below, with the understanding that secondary detector 306, arm 308, pivot joint 311 and pivot point 312 operate in the same way.

Arm 307 is coupled to the conveyance 301 by a pivot joint 309 that allows the arm 307 to rotate (or swing) about pivot point 310. In this way, the position of detector 305 may be adjusted so that it is facing the object. In some orientations, the alignment vector of secondary detector 305 may be parallel to the alignment vectors of the primary detectors 303 and 304. In such an "open" configuration (i.e., when the alignment vectors of the primary and secondary detector are substantially parallel), the system 300 will detect more of the backscattered radiation than it would with the primary detectors 303 and 304 alone. Stated alternately, the sensitivity of the system 300 to radiation scattered from the object is substantially increased when the first and second alignment vectors are substantially parallel. In some embodiments, the position of the detectors may be adjusted so that the alignment vector of each detector includes the point of scatter.

The movable arm 307 also allows the secondary detector 305 to be refracted to a position in which its alignment vector is not parallel to that of the primary detectors 303 and 304. In some embodiments, the alignment vector of secondary detector 305 may form an angle of about eighty or even ninety degrees with the alignment vector of primary detector 303. In such a "retracted" configuration, the system 300 will detect less of the backscattered radiation than it would with the secondary detector 305 in an "open" configuration. Indeed, in a "retracted" configuration, some or all of the backscattered radiation may be blocked or absorbed by other elements of the system 300, such as primary detectors 303 or 304, or the source 302.

In some embodiments, the alignment vectors of the secondary detectors may be perpendicular to the alignment vectors of the primary detectors when retracted. In such a configuration, which is illustrated by dashed arms (307' and 308') and detectors (305' and 306') in FIG. 3 and which may be known as a "closed" configuration, the sensitivity of the array is reduced (because the array itself is reduced) as compared to the open position described above, but the system is also is more compact. When a secondary detector (305 or 306) is retracted from its fully open position, a data communication channel coupled to that detector may disengage from that detector. For example, the data communication channel could be physically de-coupled from the detector, or it could be electrically turned off or its communications suspended.

A system in a closed configuration may be easier to move, and may also allow the system to be positioned closer to an object in tight quarters than the same system in an open configuration. For example, the corners 110 at the intersection of the wing 108 and fuselage 109 of the aircraft 103 schematically illustrated in FIG. 1 presents an irregular contour to the systems 101 and 102. As shown, system 102 is positioned closer to the aircraft 103 than system 101. As such, because the array of detectors 106, 107 of system 102 has been configured to be smaller than the array as configured in system 101, system 102 is able to access portions of the aircraft 103 that may not be as readily accessible to system 101 which is configured in the open position. In fact, because system 102, as configure, can get closer to the corner 110, the detectors 106, 107 of system 102 may present a large solid angle, as viewed from the corner 110, than could the array of detectors on system 101, because the array of detectors 101 is too wide to maneuver close such a corner 110. In other words, in some applications, a smaller detector array may present a larger solid angle to a point of interrogation than a larger array.

On the other hand, the detector array of system 101 may present a solid angle (from a point on the airplane 103) similar to that presented to system 102, even though system 101 is further away from the airplane. As such, system 101 may be able to detect an equal amount of backscatter radiation as a system with a smaller array, but without having to be as close to the object.

Figure 4A:
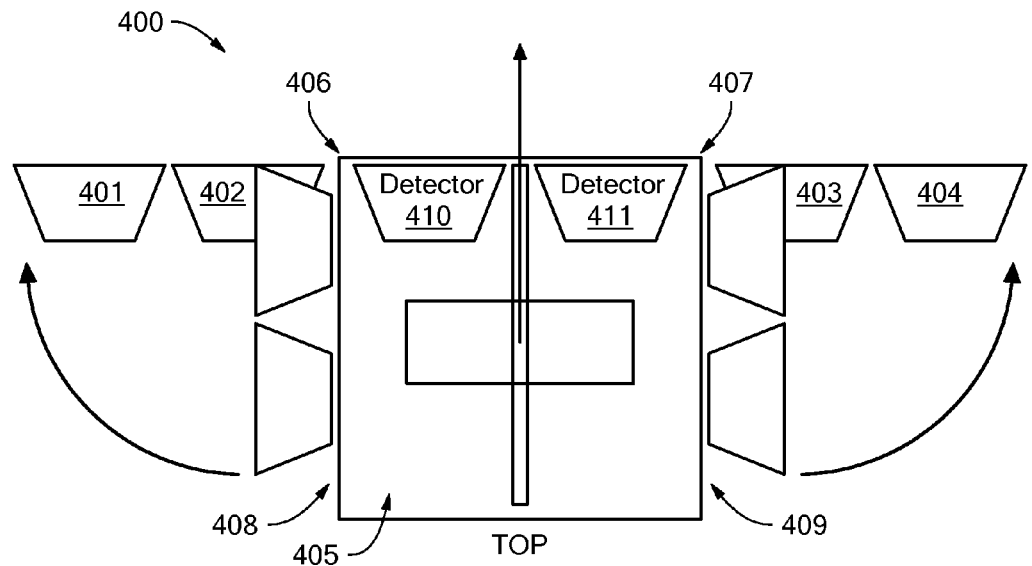
FIG. 4A and FIG. 4B schematically illustrate embodiments of variable geometry backscatter inspection systems.
Figure 4B:
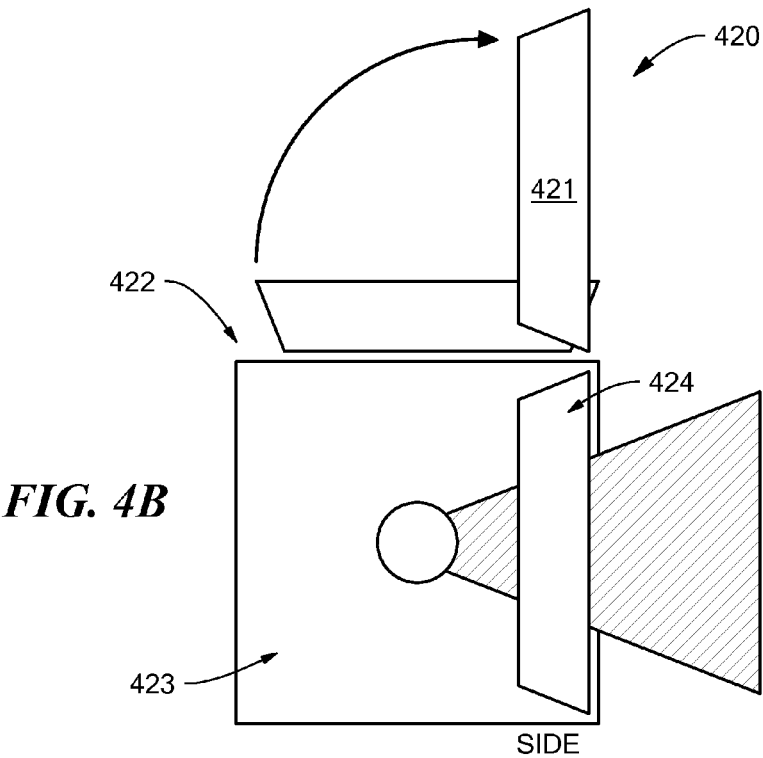

Additional embodiments are schematically illustrated in FIGS. 4A and 4B. In FIG. 4A, the system 400 is resting on the ground and viewed from a point above the system 400 looking down. Secondary detectors 401, 402, 403 and 404, each have an alignment vector, and each is movably coupled to conveyance 405 at pivot points 406 and 407 on the sides 408 and 409 of the conveyance. Pairs of detectors, such as detectors 401 and 402, may be thought of as sub-arrays, and a sub-array may have an alignment vector. In one configuration, the detector array of system 400 may be defined by moving one of the detectors 401, 402 (or a sub-array of detectors) to a position in which its alignment vector is parallel to the alignment vectors of primary detectors 410 and 411. Alternately, the size of the detector array may be reduced by moving one of the secondary detectors 401, 402 to a position in which its alignment vector is other than parallel to the alignment vector of primary detectors 410 and 411.

System 420 is schematically illustrated in FIG. 4B as resting on the ground and viewed in side profile. System 420 includes a secondary detector 421 pivotably attached to the top 422 of the conveyance. The secondary detector 421 is illustrated as a single unit, but could also be a sub-array of several detectors. In one configuration, the detector array of system 420 may be defined by moving the detector 421 into a position in which its alignment vector is parallel to the alignment vector of primary detector 424. Alternately, the size of the detector array may be reduced by moving the secondary detector 421 to a position in which its alignment vector is other than parallel to the alignment vector of primary detector 424.

Figure 5:
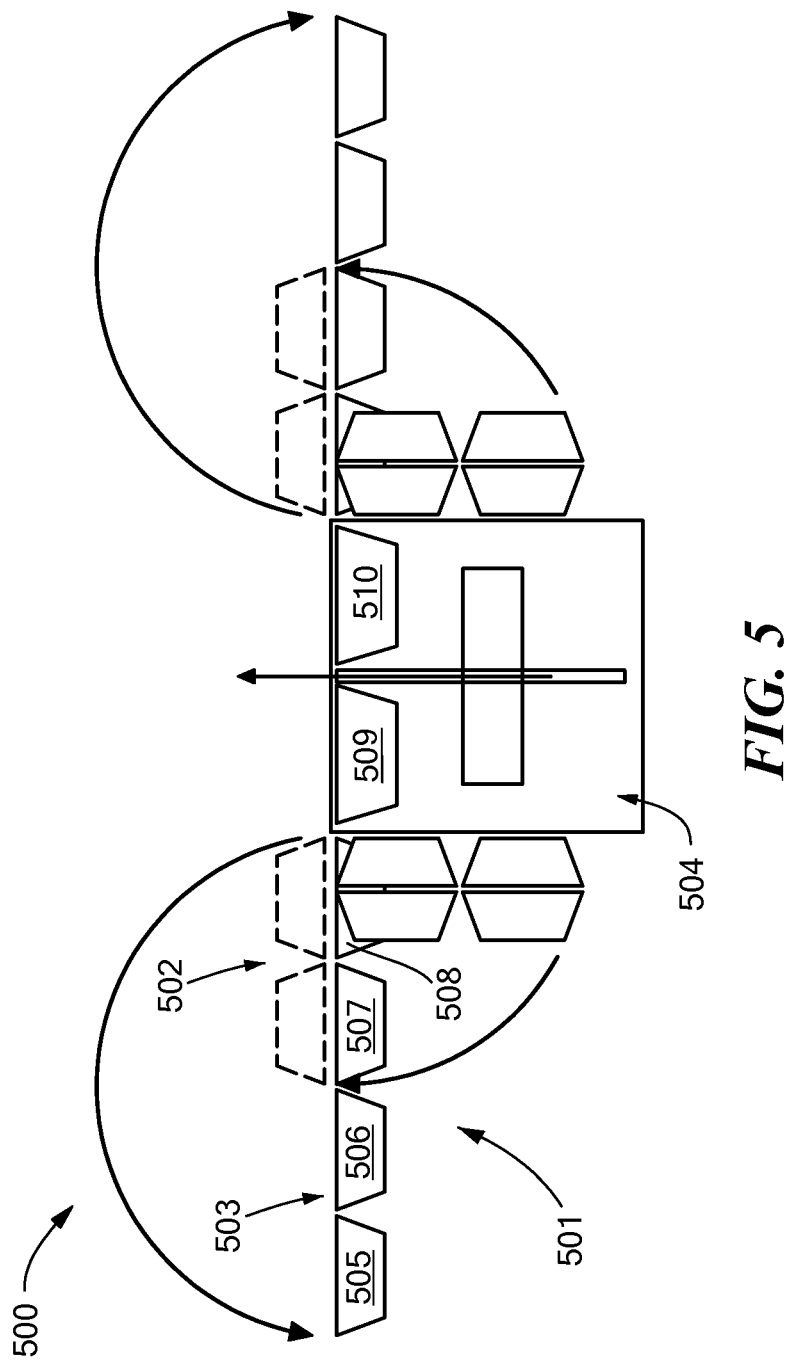
FIG. 5 schematically illustrates another embodiment of a variable geometry backscatter inspection system.

In another embodiment 500, sub-arrays may themselves be foldable, as schematically illustrated in FIG. 5. Sub-array 501 has an inner portion 502 (detectors 507 and 508) nearest the conveyance 504, and an outer portion 503 (detectors 505 and 506). In this embodiment, each portion has two detectors, and each detector has an associate alignment vector.

In an open position, the alignment vectors of detectors 505-508 are parallel to each other, and parallel to the alignment vectors of primary detectors 509 and 510. In a closed position, the alignment vectors of detectors 505-508 are not parallel to the alignment vectors of primary detectors 509 and 510. Also, in the closed position the detectors face each other in what may be termed a "clamshell" position, resulting a compact orientation. In this configuration, the alignment vectors of the secondary detectors 505 and 506 may be parallel to each other, but in opposing directions to the alignment vectors of detectors 507 and 508.

Figure 6:
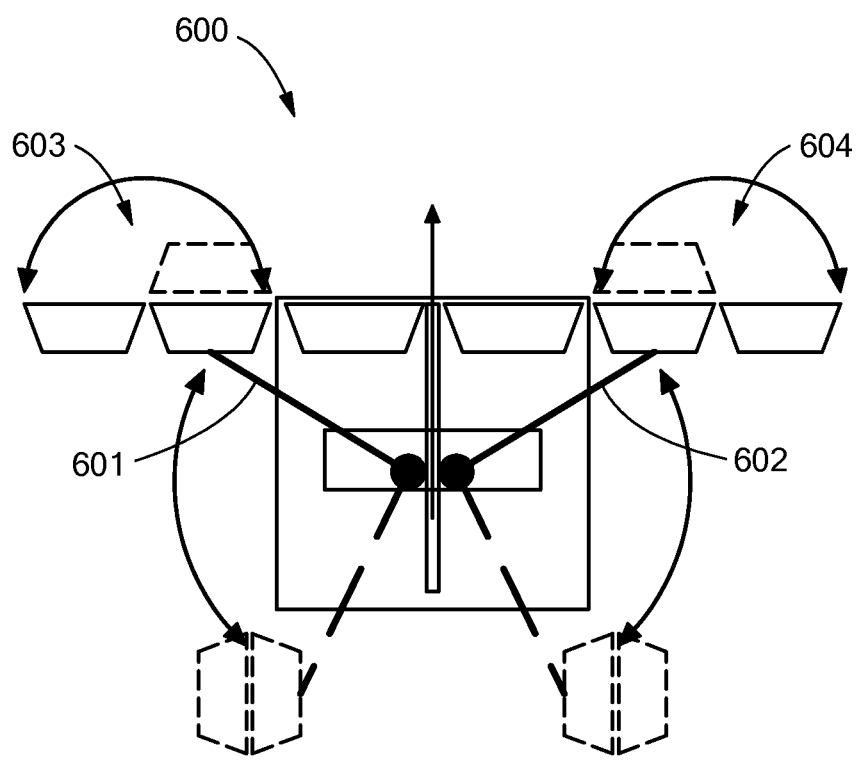
FIG. 6 schematically illustrates another embodiment of a variable geometry backscatter inspection system.

An embodiment 600 combining swinging arms 601, 602 (similar to those in FIG. 3) and foldable sub-arrays 603, 604 (similar to those in FIG. 5) is schematically illustrated in FIG. 6.

Other embodiments are schematically illustrated in FIG. 7A and FIG. 7B. In each case, secondary detector arrays are coupled to the back of a conveyance positioned on the ground.

In FIG. 7A, the system 700 is viewed from above. In this embodiment, one (701) or more (702) secondary arrays may be secured to a framework ("frame" 703, 704) that is movably coupled to a conveyance 705. By moving the frame (e.g., 703), the detectors 702A, 702B may move relative to the conveyance to be in a "closed" position (top illustration) or an "open position" (bottom illustration), or in positioned in-between. To move from the closed position to the open position, the one or more secondary array(s) slide outwards, parallel to the ground. In an alternate embodiment, also illustrated by FIG. 7A, the frame and secondary arrays may move diagonally—neither parallel to nor perpendicular to the ground.

At all times, the alignment vectors of the detectors 701A, 701B, 702A and 702B of the secondary array(s) are parallel to the alignment vectors of the primary detectors 706A and 706B, but the effective size of the system's detector array is determined by the location of the secondary arrays. Even though the respective alignment vectors of the primary and secondary detectors are parallel to each other irrespective of the location of the secondary detectors, the sensitivity of the system's detector array is likely to be greater when the secondary detector arrays are in the open position because in any other position the conveyance itself is likely to secondarily scatter or absorb some portion of the backscatter radiation that might otherwise reach the secondary detectors.

In FIG. 7B, the system 720 is viewed in side profile, and the secondary array 721 slides upwards (i.e., perpendicular to the ground) from a "closed" position (bottom illustration) to an "open" position (top illustration).

Figure 8:
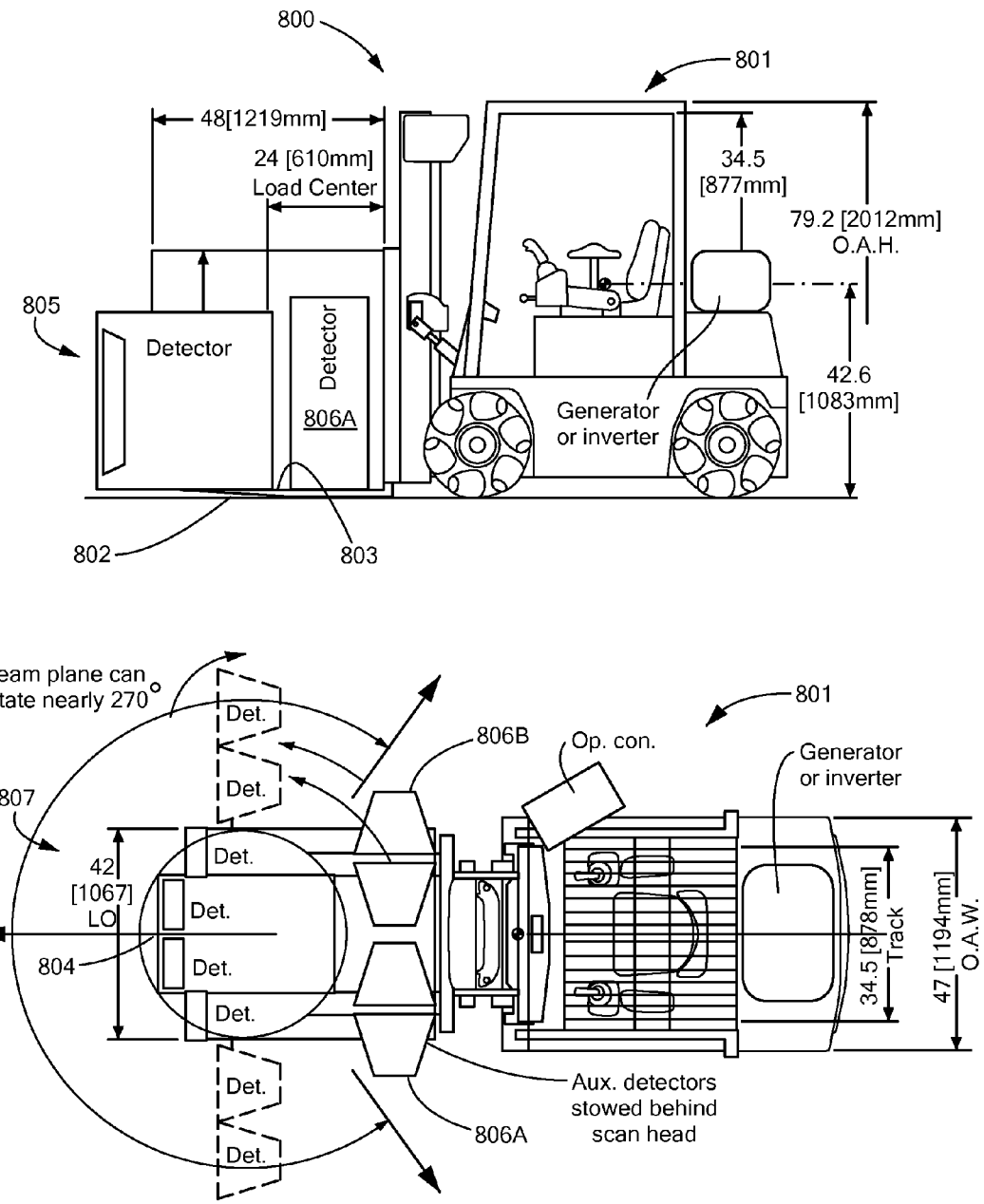
FIG. 8 schematically illustrates another embodiment of a variable geometry backscatter inspection system.

An omnidirectional forklift 801 is the conveyance in the embodiment 800 schematically illustrated in FIG. 8. The forklift 801 has a lifting platform 802 with a lifting surface 803, and may move forward and backward like a conventional forklift, but the forklift 801 can also move sideways. For example, for scanning along a large object, the forklift 801 can move sideways while the radiation source 804 and detector array 807 face the object.

The detector array 807 of system 800 includes primary detectors 805, as well as secondary detector arrays 806A and 806B. The secondary detectors 806A and 806B are movably coupled to the conveyance 801 so that their position or orientation relative to the primary detectors 805 is variable. The secondary detector arrays 806A and 806B may be implemented in ways described above, for example.

In addition, the detector array 807, along with a radiation source 804 capable of projecting a pencil beam of penetrating radiation along a transmission axis, may be rotatably attached to the forklift's lifting platform 802, such that they may rotate around an axis normal to the lifting surface 803 of the lifting platform 802, while the detectors 805, 806A and 806B, and radiation source 804, maintain a fixed spatial relationship with respect to each other.

As such, the transmission axis and the alignment axes of the detectors 805, 806A and 806B may be rotated relative to the lifting platform 802, so as to allow them to be oriented or re-oriented with respect to an object without having to move the entire system 800. In this embodiment, the beam plane/transmission axis may rotate nearly 270 degrees. For example, the radiation source 804 and detector array 807 could be rotated during a scanning operation without having to move the forklift 801.

Figure 9:
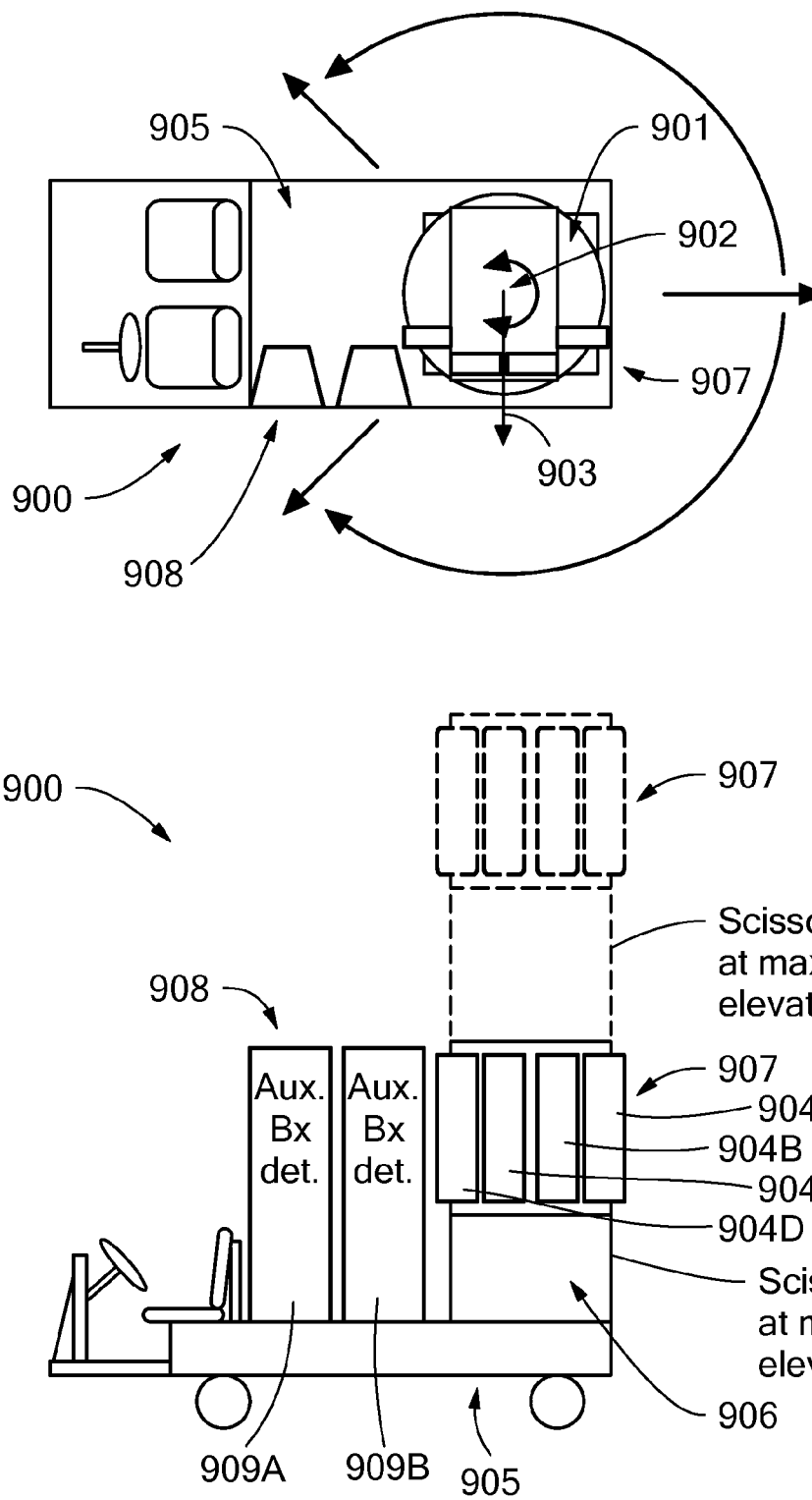
FIG. 9 schematically illustrates another embodiment of a variable geometry backscatter inspection system.

Yet another embodiment 900 is schematically illustrated in FIG. 9. System 900 includes a turntable 901 supporting a radiation source 902 that produces a pencil beam of penetrating radiation along a transmission axis 903, as well as a set of primary detectors 904A, 904B, 904C and 904D. Each of the primary detectors 904A-904D has an alignment vector, and together they form a primary array 907 that also has an alignment vector.

The radiation source 902 and primary array 907 have a fixed position relative to each other, but may rotate relative the conveyance 905 around an axis normal to the surface of the turntable 901. Some embodiments include a lifting mechanism 906, such as a scissor lift, between the conveyance 905 and the turntable 901, to enable the turntable 901 to elevate with respect to the conveyance 905.

The system 900 also has a secondary array 908 including two secondary detectors 909A and 909B. Each of the secondary detectors 909A and 909B individually, and the secondary array 908, has an alignment vector. The secondary detectors 909A and 909B are coupled to the conveyance 905 and bear a fixed spatial relationship to the conveyance 905.

In operation, primary array 907 may be rotated such that its alignment vector is parallel to the alignment vector of the secondary array 908. As such, the primary and secondary arrays may form a larger, system array. The solid angle of the combined arrays as seen from a point of backscatter is larger than the solid angle presented by the primary array 907 alone, so that the system array may be formed by rotating the primary array 907 so that its alignment vector is parallel to the alignment vector of the secondary array 908.

Figure 10:
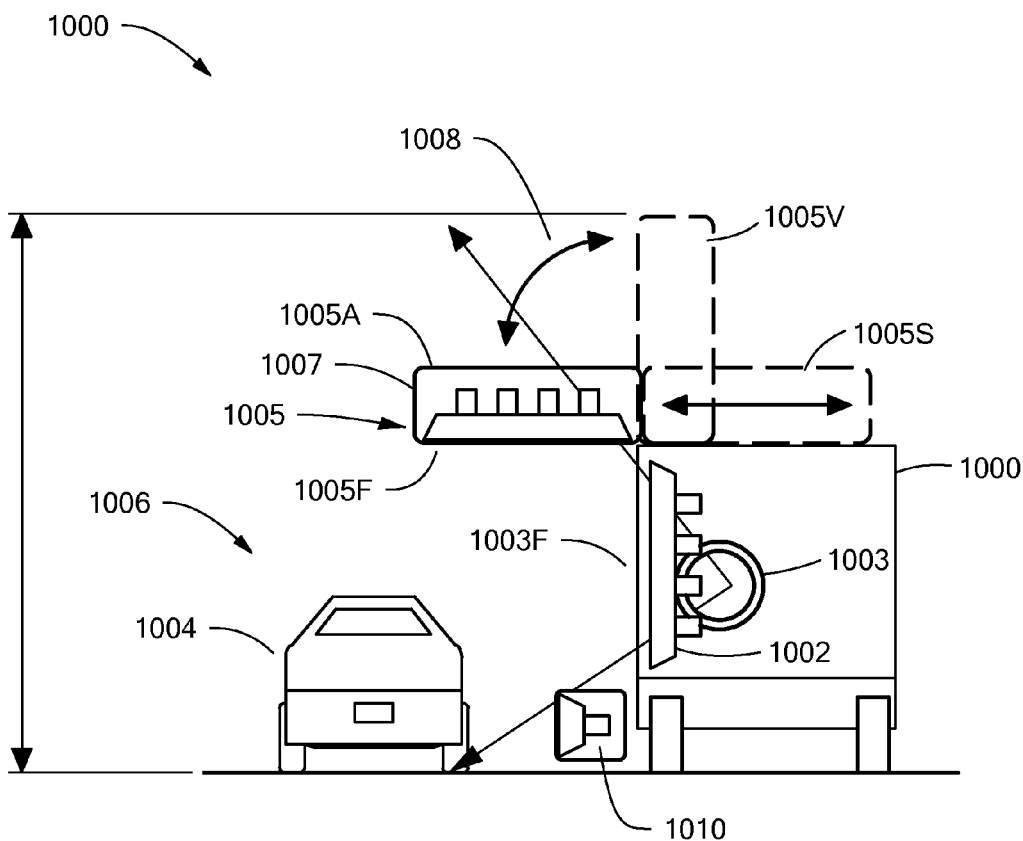
FIG. 10 schematically illustrates another embodiment of a variable geometry backscatter inspection system.

Another embodiment 1000 is schematically illustrated in FIG. 10, and includes a vehicle (or conveyance) 1001 having a first detector 1002 and an x-ray source 1003 mounted within the interior of the vehicle 1000. In this location, the first detector 1002 is configured to detect backscatter radiation from a target automobile 1004.

In in this embodiment, vehicle 1000 also has a second detector 1005 disposed on the roof of the vehicle 1000. The second detector 1005 may be protected by a weather-tight housing 1007.

The second detector 1005 may be optionally and controllably oriented so as become part of a detector array 1006, along with the first detector 1002, or moved into a stowed position 1005S, as indicated by the dashed outline of detector 1005. The second detector may be referred to as a "top-down detector," "wing detector" or "awning detector."

The second detector may be oriented in a variety of positions with respect to the vehicle and/or with respect to the first detector. In some embodiments, the second detector 1005 is slideably mounted to the vehicle, so that the second detector 1005 may be oriented from a stowed position 1005S to an awning position 1005A by sliding the second detector.

In other embodiments, the second detector 1005 may be pivotally mounted to the vehicle 1000, such that the second detector 1005 may be rotated into a variety of positions. For example, in such embodiments, the second detector 1005 may be rotated into a vertical position 1005V as indicated by the double-headed arrow 1008, such that its alignment vector is parallel to the alignment vector of the first detector 1003. In some embodiments, the face 1005F of the second detector may be coplanar with the face 1003F of the first detector. Second detector 1005 could also be rotated into stowed position 1005S.

Alternately, the second detector 1005 may be rotated into an awning position 1005A, such that its alignment vector is perpendicular, and may even intersect, the alignment vector of the first detector 1003. In addition, the second detector may be rotated to any desired angle between the awning position 1005A and stowed position 1005S.

As such, the second detector allows an operator of the system to adjust both the size and shape of the detector array, depending for example on both the size of the target vehicle and the available height clearance, and also depending on the distance between the array and the target.

Deployed horizontally as schematically illustrated as location 1005A in FIG. 10, the second detector offers several advantages. For example, the overall solid angle of the detector array 1006 is increased over the solid angle of the first detector alone (by roughly a factor of two, for the geometry shown in FIG. 10) which increases the flux (roughly in proportion to the solid angle) and the overall signal-to-noise ratio of an image produced from detected backscatter radiation.

In addition, penetration is improved beyond what would be expected from the improved signal-to-noise ratio alone. X-rays that scatter at angles closer to 90° than to 180° (i.e. X-rays that are more side-scatter than backscatter) will have higher energies. As such, in connection with an inspection of car 1004, for example, the scattered radiation is better able to escape from the metal and glass enclosure of the car 1004. The roof and trunk lid of a car are generally made of thinner steel than the sides, further enhancing the ability of scattered X-rays to escape and reach the second detector. Further, shadows created by the effective illumination from the top (i.e., an image produced from the detected scatter radiation resembles a photograph that has been lit from the top) can enhance and better enable the recognition of objects by using the shadows to highlight three-dimensional features.

The digital image in FIGS. 11A-11D illustrate the abilities of such an embodiment. Specifically, these FIGS. 11B-11D were produced using the second detector to enhance the image of a propane tank 1001 in the trunk 102 of a car, as shown in the photograph in FIG. 11A. Propane tanks in general, and most threats deep within car trunks, are considered challenges for standard backscatter imaging.

The shadowing effects discussed above can be further exploited by processing the signal from the first detector and the signal from the second detector separately, for example in separate electronic channels, because each channel will contain different shadow information.

For example, consider an appearance of the propane tank 1101 in an image 1102B generated only from scattered radiation detected by the first detector 1002, as shown in FIG. 11B. In this image, the propane tank 1101 is essentially discernible.

Next, consider the appearance of the propane tank 1101 in an image 1102C generated only from scattered radiation detected by the second detector 1005 deployed in the awning position 1005A, as shown in FIG. 11C. Here, the propane tank 1101 is more readily discernible than in an image generated from data captured by the first detector alone. As such, processing the signals from the first detector and second detector separately yields to a system operator two distinct views of the target, one of which (in this case, the image in FIG. 11B) provides a better view of the target.

Further, compare the appearance of the propane tank 1101 in an image generated from scattered radiation detected by the first detector 1002, and the second detector 1005 deployed in the awning position 1005A, as shown in FIG. 11D. Here, the image 1102D of the propane tank has a higher signal-tonoise ratio when both signals are combined, as compared to the images produced from either detector alone.

Nevertheless, the image 1102C from the second detector alone in FIG. 11C shows the strongest shadows at the bottom and side of the propane tank, which helps the viewer to see it as a distinct 3 dimensional object within the trunk of the car.

In practice, perhaps the simplest implementation would allow an operator or an image analyst to push a button to display either the combined image, or the separate first detector (which may be referred to as a "side" detector in this embodiment) or second detector (awning detector) images. For operators willing to spend more time manipulating the image, a knob or software slider bar could be used to produce a compound image by dynamically vary the mixing ratio from, for example, 100% side, 0% awning, to an equal mix of both, to 100% awning, 0% side. Producing an image by moving such a slider back and forth, and thereby dynamically changing the shadows in the image, could assist in detecting different objects hidden within a target vehicle.

Accordingly, the embodiments of FIG. 10 provide a number of potential benefits. For example, signals from the first and second detector, which may be at varying angles with respect to each other, may be processed independently, separately from one another, or may be aggregated. Further, images may be produced, based on the data from either or both of the first and second detectors. Such images may be static, or may be dynamically variable based on the contribution to a produced image from each detector. In addition, although use of the second detector, which is movable relative to the first detector, varies the size of the detector array, rather than merely changing its geometry or shape.

FIG. 10 also schematically another embodiment, including a third detector 1010, which may be referred to as an "auxiliary" detector or a "skirt" detector. The third detector 1010 is manually mounted to, and manually removable from, the vehicle 1000, and extends or supplements a detector array, such as first detector 1002 for example. Although third detector 1010 is located at the bottom of the vehicle 1010, and is may therefore also be known as a "skirt" detector, a detector array might also be extended by manually providing additional detectors around the periphery of an existing array (e.g., first detector 1002). For example, similar detectors could be mounted to the outside of the vehicle 1000 on the left or right side of the standard array. Such auxiliary detectors could be removed and stowed inside the vehicle as desire, for example for travel at speeds above the usual scan speeds or when the vehicle 1000 is left unattended.

Figure 12:
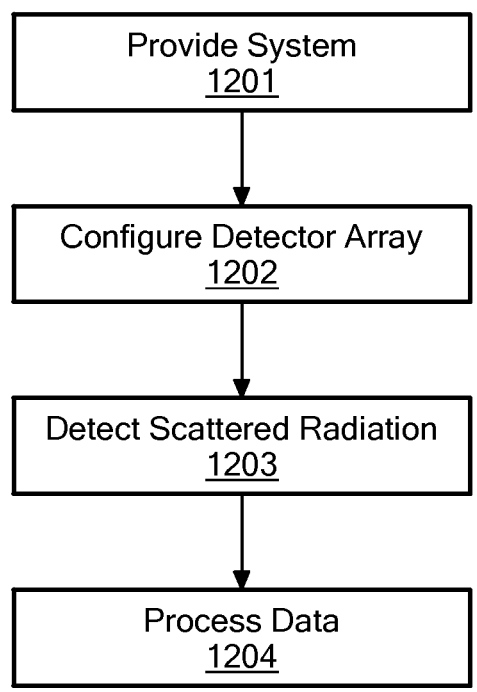
FIG. 12 is a flowchart that schematically illustrates a method of inspecting an object.

A method for inspecting an object with backscatter radiation is schematically illustrated by the flowchart in FIG. 12. Step 1201 includes providing a system with at least two detectors of backscatter radiation, where a least one of the detectors is movable and can be oriented or re-oriented relative to another detector, such as in several of the embodiments described above. Step 1202 then includes configuring the detectors to form a detector array as desired by the system's operator.

Next, the object is illuminated by a radiation source, and scattered radiation is detected at step 1203. Finally, data representing the detected radiation is processed at step 1204 to, for example, produce an image of the inspected object. The data may be processed in aggregate form, or separately, as described above.

Although various embodiments described above are described from the perspective of configuring an array, other embodiments may also be described. As noted above in connection with FIG. 1, one potential benefit of a variable geometry array that the array can be configured to be compact, thereby allowing the array to be moved closer to the object to be interrogated, and to maneuver into spaces that would not allow a larger array to approach.

For example, in FIG. 1, consider a situation in which an operator of a backscatter detector system desires to interrogate the aircraft 103 at the corner 110 formed by the wing 108 and fuselage 109. The detector array 110 is too wide to allow system 101 to maneuver into the tight space between the wing 108 and fuselage 109. However, the array of detectors 106 and 107 on system 102 are configured to that the size of the array is not as wide, and so system 102 can easily move into the between the wing 108 and fuselage 109.

In the embodiment of FIG. 1, both systems 101, 102 are on moveable bases, or conveyances. For example, systems 101 and 102 may include wheels or tracks, for example, that allow the systems 101, 102 to move along at least one line of travel. In the embodiment of FIG. 1, system 101 has a line of travel as indicated by arrow 111, and system 102 has a line of travel as indicated by arrow 112.

When viewed from a point on line of travel 111, the array 110 of system 101 presents a certain solid angle. In contrast, if the array 110 of system 101 were reconfigured into the configuration illustrated for system 102, then the array 110 would, from that same point, present a smaller solid angle. In this embodiment, such a smaller solid angle is a consequence of having reduced the size, and specifically in this case, the width of the array 110.

This allows a movable system, such as system 102, to advance a detector array along a line of travel, so as to allow the system to maneuver in tight spaces. In particular, as the system 102 moves towards the aircraft 103, the detectors do not form a wide array that might contact a portion of the aircraft, or any other nearby object, and thus prevent the system 102 from approaching the aircraft.

A system, such as systems 101 and 102, may include variable geometry arrays, including but not limited to the arrays described herein. Such a system may be described as a variable geometry backscatter inspection system for inspecting a surface of an object, including a conveyance configured to move along a line of travel, a source of a pencil beam of penetrating radiation, the source coupled to the conveyance and having an axis of emission. The system has variable geometry detector array that includes a first and second detector. The first detector has a first alignment vector, and is coupled to the conveyance such that the first alignment vector is parallel to, or capable of being configured parallel to, the line of travel. The second detector also has an alignment vector. The second detector is movably coupled to the conveyance, such that the second detector is movable between a first position and a second position, and when in the first position its alignment vector is parallel to the line of travel. As such, when viewed from a point on the line of travel, the array presents a first solid angle when the second detector is in the first position and a smaller solid angle when the second detector is in the second position.

In other words, from the perspective of a person standing on the line of travel, the approaching system can present an array of one size when the second detector is in a first position, and present an array of a smaller size when the second detector is in another position. For example, but without limitation, such a system may have variable geometry arrays as schematically illustrated in FIG. 3, FIG. 4A, FIG. 4B, FIG. 5, FIG. 6, FIG. 7A, FIG. 7B, or FIG. 8, so name but a few.

Indeed, as seen in those figures, the size of the array can be substantially reduced. In the embodiment of FIG. 3, for example, the array includes detectors 303, 304, 305 and 306. The solid angle of such an array, as seen from a point along the line of travel when all detectors are facing the same direction, includes is the combined width of those detectors. However, when detectors 305 and 306 are retracted as schematically illustrated by 305' and 306', the solid angle presented by the array, and indeed the solid angle as presented by the conveyance 301 with the array, is reduced by approximately 40 or 50 percent. Similarly, in the embodiment of FIG. 5, the array formed by detectors 505-508, along with their unenumerated counterparts on the other side of the conveyance 504, is substantially smaller when those detectors are refracted in their clamshell orientation than when they are in an open position. Indeed, in this way the solid angle presented by the conveyance 504 and array in this embodiment may be reduced by approximately 60 percent. In some embodiments, the solid angle formed by the conveyance and array of detectors may be reduced to the solid angle presented by the conveyance alone, as schematically illustrated in FIG. 7A, for example. Although various embodiments are described in terms of the relative positioning of alignment vectors, the scope of embodiments are not limited to arrays in which the alignment vectors of all detectors are parallel to each other, or to a line of travel, when in the open position.

Such systems may be distinguished from other mobile systems that have detectors or detector arrays disposed such that their alignment vectors are not oriented along the direction in which the mobile system travels. For example, a truck may have a detector (or detector array) disposed on the side of a truck, but the truck could not advance the detector in the direction of the detector's alignment vector, because a truck cannot move sideways.

A number of embodiments may be additionally described, including for example a first embodiment of a variable geometry backscatter inspection system, which includes a conveyance and a source of pencil beam penetrating radiation coupled to the conveyance. A primary detector characterized by an alignment vector is coupled to the conveyance in a first location relative to the radiation source. A secondary radiation detector characterized by a second alignment vector is coupled to the conveyance by a movable member which is movably coupled to the conveyance. As such, the alignment vector of the secondary detector is adapted for reorientation with respect to the alignment vector of the primary detector in such a manner that the sensitivity of the system to radiation scattered from the object is substantially maximized when the first and second alignment vectors are substantially parallel. In some embodiments, the movable member includes an arm with one end rotatably attached to the conveyance, and the other end coupled to the secondary radiation detector, such that the arm is rotatable between an open position in which the second alignment vector is parallel to the first alignment vector, and a retracted position in which the second alignment vector is not parallel to the first alignment vector. In alternate embodiments, the secondary detector include a first detector unit and a second detector unit the second detector unit foldable to face the first detector unit. In other embodiments, the secondary detector is coupled to the conveyance via a slidable frame, so that the secondary detector may be moved by sliding the frame parallel to the ground, perpendicular to the ground, or diagonally relative to the ground.

A variable geometry backscatter inspection system has a source of a pencil beam of penetrating radiation coupled to a conveyance. A first radiation detector has a first alignment vector and is rotatably coupled to the conveyance at a location fixed relative to the radiation source, such that the first detector rotatable between a first position and a second position. A second detector is coupled to the conveyance and has a second alignment vector, the second alignment vector parallel to the first alignment vector when the first detector is in the first position. In an alternate embodiment, the conveyance also has a lift assembly coupled to the radiation source, such that the lift assembly is extendable to raise the radiation source above the conveyance.

A method for inspecting an object includes scanning the object with penetrating radiation generated by a source disposed upon a conveyance, and detecting penetrating radiation scattered by the object onto a primary detector characterized by a first alignment vector coupled to the conveyance, and a secondary detector characterized by a second alignment vector and movable between a first position in which the second alignment vector is parallel to the first alignment vector, and a second position, wherein the sensitivity of the secondary detector to radiation scattered from the object is substantially maximized when the first and second alignment vectors are substantially parallel, and moving the secondary detector between the first position and the second position. In some embodiments, moving the secondary detector involves includes moving the secondary detector from the first position to the second position, while in other embodiments moving the secondary detector includes moving the secondary detector from the second position to the first position. Some embodiments digitize the backscatter radiation impinging on the secondary detector in a data acquisition channel during the course of inspection, and disable the data acquisition channel during the course of moving the secondary detector out of the first position. In some embodiments, disabling the data acquisition channel includes electrically disconnecting the data acquisition channel.

In addition, the foregoing disclosure can support a number of potential claims, such as those listed below.

P1. A variable geometry backscatter inspection system comprising:

a conveyance; a source of a pencil beam of penetrating radiation, the source rotatably coupled to the conveyance; a first detector rotatably coupled to the conveyance, the first detector having a fixed location relative to the radiation source and a first alignment vector, the first detector rotatable between a first position and a second position; and a second detector coupled to the conveyance and having a second alignment vector, the second alignment vector parallel to the first alignment vector when the first detector is in the first position.

P2. The variable geometry backscatter inspection system of potential claim P1, the conveyance further comprising a lift assembly coupled to the radiation source, whereby the lift assembly is extendable to raise the radiation source above the conveyance.

P3. A method for inspecting an object, the method comprising: scanning the object with penetrating radiation generated by a source disposed upon a conveyance; detecting penetrating radiation scattered by the object onto a primary detector coupled to the conveyance, the primary detector characterized by a first alignment vector; detecting penetrating radiation scattered by the object onto a secondary detector, the secondary detector characterized by a second alignment vector and movable between a first position in which the second alignment vector is parallel to the first alignment vector, and a second position, wherein the sensitivity of the secondary detector to radiation scattered from the object is substantially maximized when the first and second alignment vectors are substantially parallel; and moving the secondary detector between the first position and the second position.

P4. The method for inspecting an object of potential claim 3, wherein moving the secondary detector comprises moving the secondary detector from the first position to the second position.

P5. The method for inspecting an object of claim potential claim 3, wherein moving the secondary detector comprises moving the secondary detector from the second position to the first position.

P6. The method for inspecting an object of claim potential claim 3, further comprising digitizing the backscatter radiation impinging on the secondary detector in a data acquisition channel during the course of inspection and disabling the data acquisition channel during the course of moving the secondary detector out of the first position.

P7. The method of inspecting an object of potential claim 6 wherein disabling the data acquisition channel comprises electrically disconnecting the data acquisition channel.

The embodiments of the invention described above are intended to be merely exemplary; numerous variations and modifications will be apparent to those skilled in the art. All such variations and modifications are intended to be within the scope of the present invention as defined in any appended claims.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods may be implemented as a computer program product for use with a computer system. Such implementation may include a series of computer instructions fixed either on a tangible medium, such as a non-transient computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software.

What is claimed is:

1. A variable geometry backscatter inspection system for inspecting a surface of an object, the system comprising:
   a conveyance configured to move along a line of travel;
   a source of a pencil beam of penetrating radiation, the source coupled to the conveyance and having an axis of emission;
   a variable geometry detector array, the array comprising:
      a first detector coupled to the conveyance and having a first alignment vector, the first alignment vector parallel to the line of travel;
      a second detector movably coupled to the conveyance and having a second alignment vector, the second detector movable between a first position and a second position, wherein the second alignment vector is parallel to the line of travel in the first position;
   such that the array presents a first solid angle when viewed from a point on the line of travel when the second detector is in the first position, and a smaller solid angle when the second detector is in the second position.

2. The variable geometry backscatter inspection system of claim 1, wherein the second detector movably coupled to the conveyance by a movable member.

3. The variable geometry backscatter inspection system of claim 1, wherein the movable member comprises an arm, the arm comprising:
   a first end rotatably coupled to the conveyance; and
   a second end coupled to the second detector.

4. The variable geometry backscatter inspection system of claim 1, wherein the second detector comprises a first unit and a second unit, the second unit foldable to face the first unit.

5. The variable geometry backscatter inspection system of claim 2, wherein the movable member comprises:
   a detector frame defining the second alignment vector parallel to the first alignment vector, and movable with respect to the conveyance such that the second alignment vector remains parallel to the first alignment vector in both the first and second position.

6. The variable geometry backscatter inspection system of claim 5, wherein the detector frame is adapted for motion parallel to a surface on which the conveyance is located.

7. The variable geometry backscatter inspection system of claim 5, wherein the detector frame is adapted for motion perpendicular to a surface on which the conveyance is located.

8. The variable geometry backscatter inspection system of claim 5, wherein the detector frame is adapted for motion diagonally with respect to a surface on which the conveyance is located.

9. A variable geometry backscatter inspection system for inspecting a surface of an object, the system comprising:
   a conveyance;
   a source of a pencil beam of penetrating radiation, the source coupled to the conveyance;
   a primary detector coupled to the conveyance, the primary detector having a first location relative to the radiation source and a first alignment vector;
   a movable member movably coupled to the conveyance; and
   a secondary detector coupled to the movable member, the secondary detector having a second alignment vector,
   such that the alignment vector of the secondary detector is configured for reorientation with respect to the alignment vector of the primary detector in such a manner that the sensitivity of the system to radiation scattered from the object is substantially maximized when the first and second alignment vectors are substantially parallel.

10. The variable geometry backscatter inspection system of claim 9, wherein the movable member comprises an arm, the arm comprising:
    a first end rotatably coupled to the conveyance; and
    a second end coupled to the secondary detector;
    such that the arm rotatable between an open position in which the second alignment vector is parallel to the first alignment vector, and a retracted position in which the second alignment vector is not parallel to the first alignment vector.

11. The variable geometry backscatter inspection system of claim 10, wherein the second alignment vector is perpendicular to the first alignment vector when the second end is in the retracted position.

12. The variable geometry backscatter inspection system of claim 10 wherein the secondary detector comprises a first unit and a second unit, the second unit foldable to face the first unit.

13. The variable geometry backscatter inspection system of claim 9, wherein the movable member comprises:
 a detector frame defining a secondary alignment vector parallel to the first alignment vector and movable with respect to the conveyance such that the secondary alignment vector remains parallel to the first alignment vector.

14. The variable geometry backscatter inspection system of claim 13, wherein the detector frame is adapted for motion parallel to a surface on which the conveyance is located.

15. The variable geometry backscatter inspection system of claim 13, wherein the detector frame is adapted for motion perpendicular to a surface on which the conveyance is located.

16. The variable geometry backscatter inspection system of claim 13, wherein the detector frame is adapted for motion diagonally with respect to a surface on which the conveyance is located.

17. A method for inspecting an object with backscatter radiation, the method comprising:
 providing a conveyance comprising a source of a pencil beam of penetrating radiation;
 providing a first detector of backscatter radiation, the first detector having a fixed position relative to the conveyance, and the first detector having a first alignment vector;
 providing a second detector of backscatter radiation, the second detector movably coupled to the conveyance, and the second detector having a second alignment vector;
 orienting the second detector such that the second alignment vector intersects the first alignment vector;
 illuminating the object with a pencil beam of radiation from the source;
 detecting radiation scattered by the source with the first detector and the second detector;
 generating a first image of the object using data representing the radiation scattered by the source and detected by the first detector; and
 generating a second image of the object using data representing the radiation scattered by the source and the second detector.

18. The method of claim 17, further comprising producing a compound image by combining data from the first image with data from the second image.

19. The method of claim 18, wherein producing a compound image by combining data from the first image with data from the second image includes producing a dynamically variable image by adjusting the proportion of the first image and the proportion of second image combined to produce the compound image.

20. The method of claim 17, wherein orienting the second detector such that the second alignment vector intersects the first alignment vector comprises orienting the second detector such that the second alignment vector intersects the first alignment vector the angle at a right angle.

* * * * *